(12) United States Patent
Friswell et al.

(10) Patent No.: US 6,846,680 B2
(45) Date of Patent: Jan. 25, 2005

(54) LIQUID HANDLING SYSTEM WITH AUTOMATICALLY INTERCHANGEABLE CANNULA ARRAY

(75) Inventors: David R. Friswell, Upton, MA (US); Raymond Dunlap, Uxbridge, MA (US); George Grubner, Needham, MA (US); Enrique Bernal, Westborough, MA (US)

(73) Assignee: Caliper Life Sciences, Inc., Mountain View, CA (US)

( * ) Notice: Subject to any disclaimer, the term of this patent is extended or adjusted under 35 U.S.C. 154(b) by 380 days.

(21) Appl. No.: 09/918,858

(22) Filed: Jul. 31, 2001

(65) Prior Publication Data

US 2003/0027345 A1 Feb. 6, 2003

(51) Int. Cl.[7] .................................................. B01L 3/02
(52) U.S. Cl. ........................ 436/180; 422/65; 422/100; 73/864.14; 73/864.17
(58) Field of Search .......................... 436/180; 422/100, 422/65; 73/864.14, 864.17

(56) References Cited

U.S. PATENT DOCUMENTS

| | | | | |
|---|---|---|---|---|
| 3,650,306 A | * | 3/1972 | Lancaster | .................... 141/238 |
| 5,497,670 A | * | 3/1996 | Carl | .......................... 73/863.32 |
| 6,589,483 B1 | * | 7/2003 | Maeda | ........................ 422/100 |
| 2001/0039843 A1 | | 11/2001 | Schoeppe | |
| 2002/0051737 A1 | * | 5/2002 | Sollbohmer et al. | ......... 422/100 |

OTHER PUBLICATIONS

CyBio AG "CyBi Well 384/1536" *CyBio AG Information Brochure* 1pg.
Stanchfield, Jim, "Laugh at Plate Crashes with Duraflex Hydra Needles" *Robbins Scientific* (2000) 8 (1):1–5.
Zymark Corporation "Advanced Liquid Handling" *SciClone Automated Liquid Handler Brochure* (2000): 4pgs.

\* cited by examiner

*Primary Examiner*—Jan M. Ludlow
(74) *Attorney, Agent, or Firm*—Donald R. McKenna

(57) ABSTRACT

The present invention provides a liquid handling system capable of automated dispensing and reformatting operations by virtue of a quick-release cannula array mounting system that permits cannula arrays to be changed automatically by the system or manually by a user. Automated changing of the cannula array is carried out by relative movement of the dispensing head and the sample support surface to deliver the attached cannula array to a storage location, releasing the array from the dispensing head, and attaching a new cannula array. Relative movement between the dispensing head and sample support surface in at least two dimensions increases flexibility of the system and makes self-loading of the cannula array practical. The system provides advantages in time and accuracy of cannula array changeover procedures. The automated cannula array changeover capability permits automated wellplate reformatting procedures, which can be performed quickly and accurately.

36 Claims, 9 Drawing Sheets

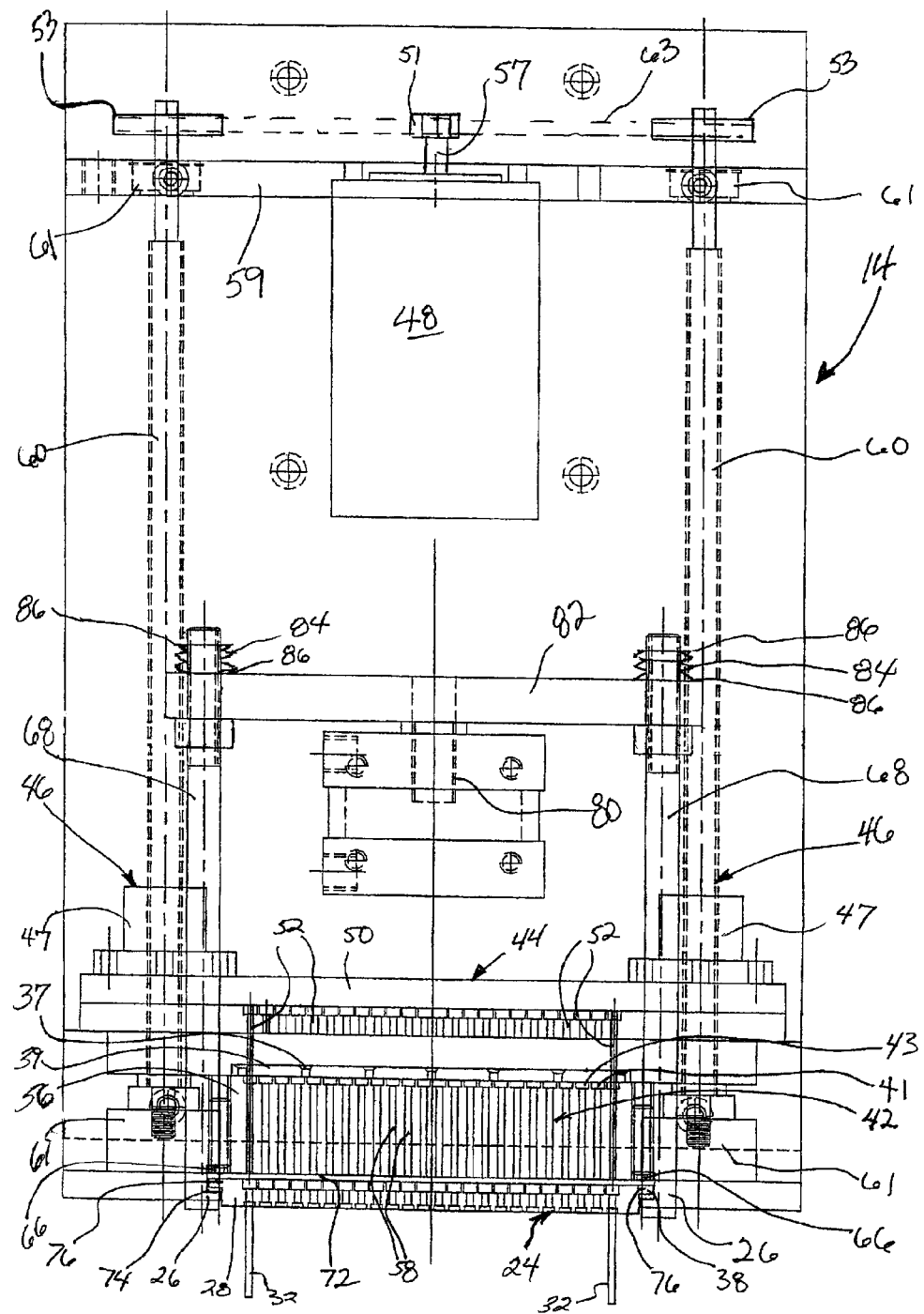

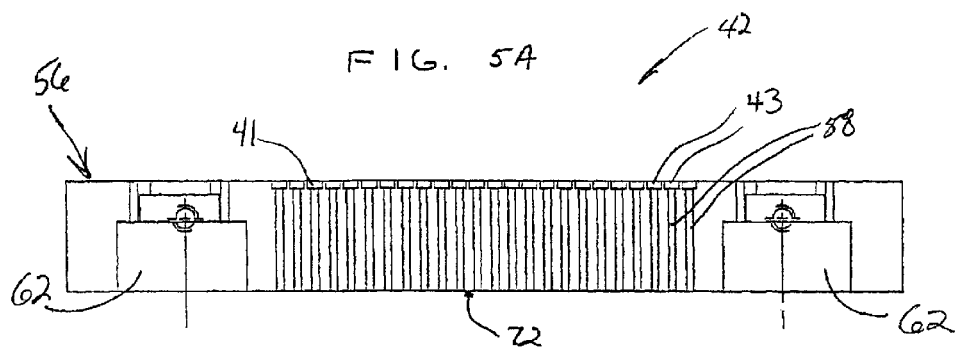
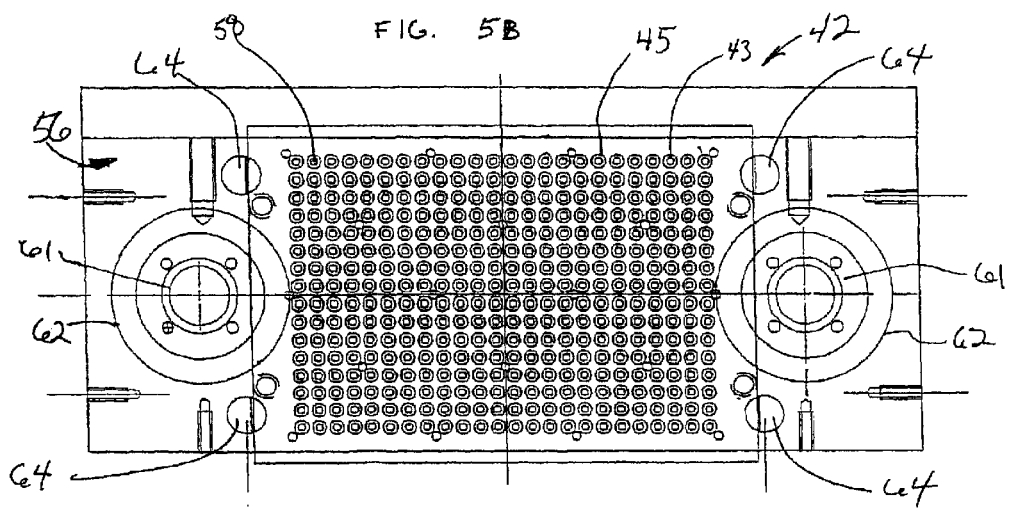
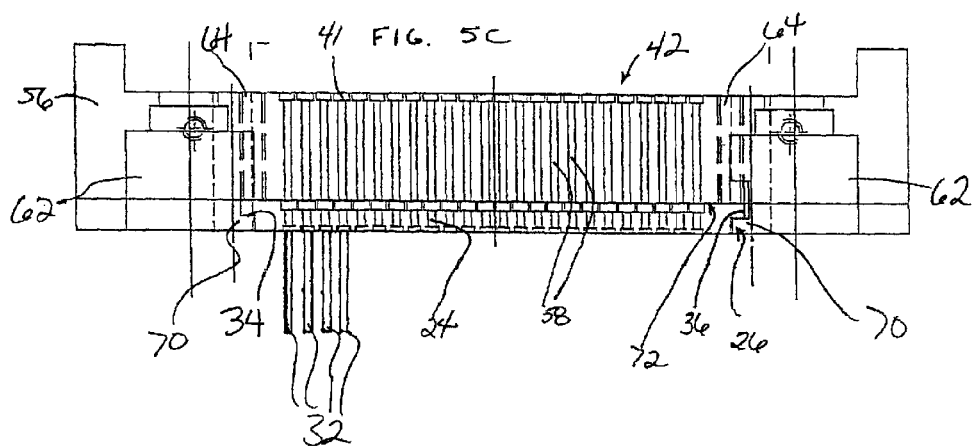

FIG. 6
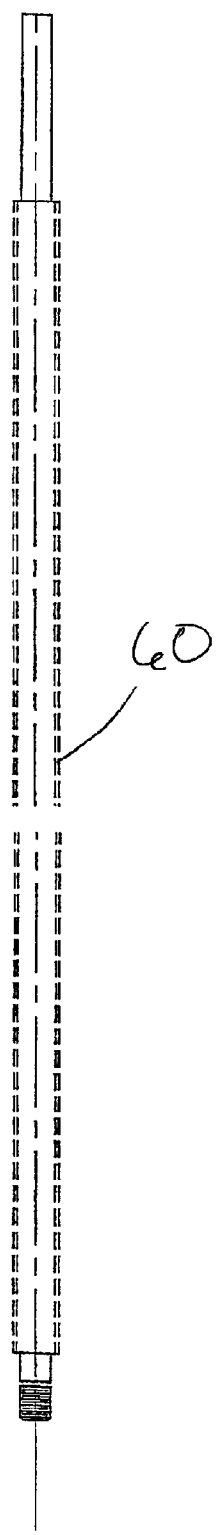
60
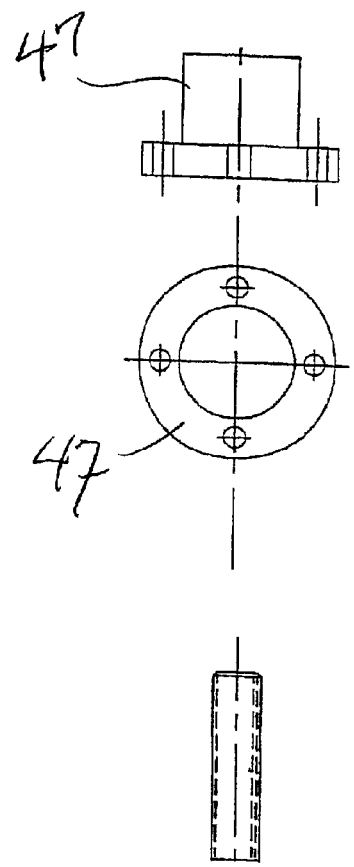
47
FIG. 7A
47
FIG. 7B
FIG. 8
68
74

LIQUID HANDLING SYSTEM WITH AUTOMATICALLY INTERCHANGEABLE CANNULA ARRAY

FIELD OF THE INVENTION

The present invention pertains to the field of automated liquid handling systems.

BACKGROUND OF THE INVENTION

Automated liquid handling systems are designed to aspirate or dispense minute, accurate quantities of liquid for the purpose of transferring liquid from one reservoir to another. The systems are configured to aspirate liquid from and dispense liquid to standardized liquid reservoirs known as wellplates, which are configured to hold biological or chemical samples, usually suspended in a neutral liquid medium. Liquid handling systems comprise a dispensing head having one or more fluid pathways through which is controlled the dispensing of the liquid and a support surface for holding the wellplates in proximity to the dispensing head. The dispensing head and/or the support surface are configured to move relative to each other in at least one or more dimensions to facilitate dispensing and transfer of wellplates through the dispensing area.

The fluid pathways of the dispensing head are pressurizable to control the flow of liquids being handled. The fluid pathways may be in communication with an external source of pressure or may be configured to have individual pumping capability such as by having individual pumping chambers integrated therein. In one example of a liquid handling system, the pumping chambers may be defined by an array of syringe bodies that are operated in unison by the system to aspirate and dispense liquid through an array of multiple dispensing tips or cannulas in fluid communication with the syringe bodies. The cannula array corresponds to the number and arrangement of syringe bodies. The liquid handling system is operated by moving the dispensing head to a source wellplate, lowering the cannulas into liquid contained in the wells and operating the syringes to aspirate liquid into the cannula tips. The dispensing head then is repositioned over a destination wellplate, the cannulas lowered into the wells and liquid dispensed. An advantage offered by automated liquid handling systems is an increase in efficiency offered by the simultaneous operation of multiple cannulas versus manual liquid sample handling conducted by lab technicians using single pipettes to fill or aspirate samples from individual wells.

Automated liquid handling systems are useful in the biotechnology and pharmaceutical industries where numerous organic samples must be mixed and stored during their testing. Such testing is especially cumbersome in research involving proteins in which numerous samples are mixed in a biologically compatible solution, such as Dimethyl Sulfoxide (DMSO). By providing an automated way to dispense a common liquid into a plurality of sample wells, the liquid handling system greatly reduces the amount of time and labor needed to accomplish large scale testing of the various organic compounds. In automating the operation of a liquid handling system, provisions may be made to dispense liquid into multiple wellplates without requiring human intervention to place and align the plates in the path of the dispensing head of the system. Reducing the amount of human intervention necessary between wellplate preparations is significant due to the high number of sample preparations required in the scientific evaluation of various experimental compounds.

Various improvements have been made to automated liquid handling systems to increase the number of samples that may be prepared before human intervention is required to reload or reset the equipment. First, the number of sample wells defined on a single wellplate and corresponding cannulas have increased. Industry standards for the numbers of wells in a wellplate have increased over the years from 4 to 96 to 384 to 1,536 well systems. The dimensions of the wellplates remains the same standardized size despite the increase in the number of wells per plate, requiring that the volume of each well be decreased accordingly and arrangement density be increased. In addition, dispensing heads can be configured to have a removable cannula array that can be reconfigured so that different size wellplates (96, 384, 1536) can be more efficiently serviced by the liquid handling system by simply changing the cannula array to a different configuration. However, although the efficiency in the number of samples increases by increasing the array size, problems in dealing with clogging and misdispensing also become more complicated as the array size and density increase.

Clogging of one or more of the cannulas, though may be detectable by computer software of the dispenser controller monitoring the syringe bodies, still can be difficult to correct in a large array system. Removal of and replacement of a cannula array can introduce fluid pathway sealing problems or misalignment of the array that can cause the cannulas to "crash" into a wellplate when it is lowered if the cannulas miss their intended wells. Additionally, in systems that use disposable plastic tips in place of cannulas, expensive replacement tips must be maintained on hand for such service of the arrays. If the cannula array is bolted to the syringe body platform of the dispensing head, the task of aligning the array can become a difficult, time-consuming job requiring a high degree of operator skill to achieve proper alignment.

A useful operation performed by the liquid handlers described above is plate reformatting of wellplates containing existing samples to new wellplates having a higher well density to reduce the space required to store samples. Samples stored in wellplates having 96 wells may be aspirated and transferred by the dispensing head to wellplates having 384 or 1536 wells per plate. In this manner, samples previously contained on several low-density source plates can be combined onto a single high-density destination plate, easing storage requirements for the laboratory. Accordingly, as laboratories strive to maximize the efficiency with which sample storage space is used, a common task that must be performed is reformatting of existing source wellplates to higher density wellplates to more efficiently store and process the samples. Due to the numerous compounds that need to be tested in biological experiments, sample mixing and reformatting procedures are run for extensive periods without interruption in order to keep up with the demand for sample preparation and maintenance.

Currently liquid handling devices are available that are configured to permit reconfiguration of the cannula array. The CyBio CyBi-Well 384/1536 liquid handler available from CyBio AG, Goschwitzer STR. 40, DD7745, Jena, Germany (also available as the Matrix PlateMate 96/384 automated pipette) is configured to provide a removable dispensing head unit that may be interchanged with head units of different cannula array configurations. The head is removably maintained in place by brackets that engage the head unit and are movable by an electric solenoid to lock the head in place during use. However, the dispensing head of the CyBio device does not permit changing only the cannula configuration, but also requires that the syringe body array also be changed with the head unit if the format is to be changed. Additionally, the Cybio device is not fully automated. An operator must load and unload the head units after being unclamped from the device. Additionally, the operator must peel-away a disposable gasket material that overlies the multiple plastic cannulas that serve as dispensing tips. The gasket material must be reapplied when reinstalling the head unit.

A dispensing head having an interchangeable cannula array is desirable for other reasons in addition to facilitating reformatting procedures. If small quantities of liquid are to be dispensed into high-density wellplates, shorter, smaller diameter cannulas are preferably fitted to the dispensing head. The shorter, smaller diameter cannulas are desirable because the smaller volume they define facilitates accurate metering of minute quantities of liquid. Also the smaller cannula tips are easier to align with the high-density wellplate. Another situation that may require changing the cannulas of the dispensing system arises when clogging in one or more of the cannulas is detected. Also, it may be necessary to change the cannula array if cross-contamination of any of the cannula tips by the sample liquids has occurred.

The capacity of a liquid handling system may also be increased by automating the movement of the dispensing head relative to the wellplates. Automating movement can be accomplished by either imparting a movement mechanism to the dispensing head, or to the support surface for a plurality of wellplates or to both. Liquid handling systems that employ an automated movable support surface to move multiple wellplates into position under the dispensing head are available in the CyBio device mentioned above and also in the Zymark SciClone FD series liquid handler. Both provide a movable support surface to transfer wellplates beneath the dispensing head in addition to providing dispensing head movement. The systems provide automated movement of the support surface along a single axis of movement. Additional robotic components may be added to the system that can transfer a series of wellplates from an adjacent storage location, such as a stacking tower, to the movable support surface then retrieve wellplates from the support surface that have been processed and return them to the storage location.

Independent movement of the dispensing head by robotic actuators provides displacement relative to the sample support surface necessary to reach multiple wellplates. The CyBio device provides a system capable of movement in two dimensions. However, the Zymark SciClone and another liquid handling device available under the trade name Biomek FX available from Beckman Coulter of 4300 North Harbor Boulevard, Fullerton, Calif., provide liquid handling systems with dispensing head movement in three dimensions. Three-dimensional movement of the dispensing head provides greater range of motion and positional accuracy.

To aid in the processing of samples by liquid handling systems, it would be desirable to provide a system capable of automatically accessing wellplates from different locations and capable of automatically changing the cannula array format of the dispensing head with minimal or no human assistance. Also, to take advantage of a reconfigurable array system and to facilitate servicing of the cannulas, it would be desirable to provide a quick-release cannula array mounting system that permits a user to quickly change a cannula array while insuring its proper alignment with the fluid pathway of the dispensing head and the wellplates that are to be serviced by the array. An object of the present invention is to provide such a system.

SUMMARY OF THE INVENTION

The present invention provides a liquid handling system capable of automated dispensing and reformatting operations by virtue of a quick-release cannula array mounting system that permits cannula arrays to be changed automatically by the system or manually by a user. The liquid handling system comprises a dispensing head, a sample support surface and a quick-release mounting system capable of releasably securing a cannula array to the dispensing head. The cannula array comprises a plate supporting a plurality of cannulas extending from one side of the plate in a perpendicular orientation relative to the plate and having the other side of the plate configured to interface with a fluid pathway of the dispensing head. Automated changing of the cannula array is carried out by moving of the dispensing head to deliver the attached cannula array to a storage location, releasing the array, and attaching a new cannula array. Relative movement between the dispensing head and sample support surface along at least two-dimensional axes increases flexibility of the system and makes self-loading of the cannula array practical. The system provides advantages in time and accuracy of cannula array changeover procedures. The configuration of the inventive system permits automated changeovers that can be performed more quickly and accurately than was previously possible, with or without human intervention.

In one aspect of the invention, a quick-release mounting system for securing a cannula array is provided to facilitate removal and attachment of the cannula array to the dispensing head, either manually or automatically. The quick-release mounting system and procedure for cannula array mounting simplifies service and maintenance of the dispensing system so that problems such as clogging are more easily addressed. Also, wellplate reformatting, in which samples are transferred from low density array format wellplates to wellplates having higher density formats (96 to 384 or 1536) are also expedited. Such reformatting procedures are more efficiently carried out when an appropriate cannula array that maximizes the number of cannulas that can fit in the source wellplate is employed on the dispensing head. A quickly interchangeable cannula array system is advantageous in providing easy array changes that require little or no operator involvement. In the present system, a cannula array can be placed into position in the dispensing head, then locked into place, fully aligned, either manually, or automatically by movement of the support surface or dispensing head to position the head over the array and actuation of the quick-release mounting system to engage the array.

The quick-release mounting system for the cannula array may be configured in various ways. However, the quick-release system should permit loading and proper alignment of the array with the dispensing head by simple movement of the array into position. Simplified movement entails a minimum of steps and relative movement between the array and dispensing head in order to achieve loading and proper alignment between them. Either the cannula array may be moved and loaded onto a stationary dispensing head, or the dispensing head may moved into position over a stationary cannula array to accomplish loading. Proper positioning of the cannula array on the dispensing head requires that the opening of each cannula align with a defined fluid pathway of the dispensing head. Fluid pathways of the dispensing head may be defined by individual syringe bodies. Sealing elements such as individual rubber O-ring gaskets or a sealing mat of silicone rubber are provided between the syringe bodies and cannulas to insure an effective fluid tight seal between the fluid pathways defined by those components when the mounting system is secured. Additionally, the system may be configured to provide a mechanism to urge the array away from the dispensing fluid pathway to break the seal formed during engagement and ensure complete ejection of the cannula array.

It is preferred that the array be loaded into position on the dispensing head in as few steps as possible, such as sliding or snapping into position with confirmation of alignment being made obvious by a positive engagement. The quick-release configuration may include guides and/or positive locating stops, such as alignment pins, to ensure proper alignment of the plate with the fluid pathways of the dispensing head and thus with the wellplates it will service. The system should align the plate with the fluid pathways of the dispensing head, without intensive labor being required by an operator. Simplified installation and removal not only reduces time and labor needed to change over an array by an operator, but it also enables automated changeover procedures, conducted without operator involvement.

The quick-release mounting system may comprise a releasable clamp as well as a bracket or a plate mounted onto the bottom of the dispensing head or on the cannula array to align the array with the dispensing head during loading. The clamp may comprise one or more clamping rods arranged on the dispensing head that are configured to engage the cannula array then be moved by an actuator to secure the array to the dispensing head.

In a preferred embodiment, for alignment of the array, the quick-release system includes an L-shaped bracket joined to or formed on the bottom of the dispensing head, which forms opposing L-shaped grooves into which the plate of the cannula array can slide. Alignment pins provided on the L-shape bracket correspond to alignment recesses on the array plate so that when the pins and recesses engage, the array plate is properly positioned in the grooves relative to the fluid pathway defined in the dispensing head. To lock the cannula array into position on the dispensing head, the quick-release mechanism further comprises a clamp that may be automatically actuated to capture the cannula array aligned on the L-shaped grooves and lock it into position. The clamp may form, at least partially, a portion of the L-shaped bracket in that the clamp comprises clamping rods having a notch that corresponds with the groove of the L-shaped bracket. Actuating the clamping rods raises them, elevating the notch and the cannula array plate captured therein, brining the plate into engagement with the dispensing head.

Another embodiment of the quick-release mounting system is configured to load and secure a cannula array by relative movement between the dispensing head and support surface in one dimension. In the alternate system, the L-shaped bracket is eliminated in favor of pilot rods mounted to the cannula array that become engaged with the clamping rods to effect alignment and securement of the array to the dispensing head. The pilot rods correspond in number and placement to the clamping rods. By relative movement of the dispensing head and support surface the pilot rods are aligned with releasable locking mechanisms at the ends of the clamping rods so that engagement can be effected. After the clamping rods become engaged with the pilot rods, the clamping rods can be actuated to lift the cannula array plate into sealed engagement with the dispensing head.

Various quick-release locking mechanisms can be employed at the ends of the clamping rods to capture the pilot rods. In one embodiment, the locking mechanism comprises opposed hinged clamp arms that close around a cap head portion of the pilot rods when the clamping rods are elevated. Another quick release locking mechanism employs locking balls captured between inner and outer sleeves of the clamping rods. The balls may be selectively advanced into a cavity defined by the inner sleeve to engage the cap head ends of the pilot rods to effect engagement.

The clamp mechanism, such as the clamping rods, may be operated to secure the cannula array by an actuator. One type of actuating mechanism that can be remotely and automatically controlled, such as by a computer, is a pneumatically operated piston configured to move the clamp to effect locking of the cannula array to the dispensing head. Other mechanisms for effecting locking engagement between the bracket and the cannula array may include an electric solenoid, electric stepper motors driving threaded components, or hydraulic actuators to name a few. The quick-release system for the cannula array not only makes automated loading of the array possible, but also expedites manual loading and unloading of cannula arrays by an operator. The expedited loading hastens changeover procedures and troubleshooting of problems such as cannula tip clogging.

In another aspect of the invention, the liquid handling system employs relative movement of the dispensing head and sample support surface to accomplish automated loading of cannula arrays onto the dispensing head. Preferably, movement of the dispensing head in three dimensions (along the X, Y and Z axes) is provided. Movement of the sample support surface in one or more dimensions relative to the dispensing head also may be provided in addition to or alternatively to three-dimensional dispensing head movement. However, loading of a cannula array onto the dispensing head may be accomplished by relative movement between the head and support surface in only one dimension. Automated operation of the system in which a series of wellplates may be serviced without human intervention is best accomplished by relative movement in at least two dimensions. In a preferred embodiment, the dispensing head is moved through a three-dimensional range of motion by robotics comprising electric motor drives of conventional design, commonly used in the liquid handling system art. A commercially available dispensing system incorporating such a three-dimensional dispensing head movement and exemplary driving hardware is the Zymark SciClone FD liquid handler, available from Zymark Corporation, Zymark Center, Hopkinton, Mass.

The movement of the dispensing head in three-dimensions serves to extend the automated operation time of the dispensing system in several ways. In one aspect, the three-dimensional movement of the dispensing head permits the access of multiple wellplates located around the wellplate support surface that lies beneath a dispensing head. Fore and aft and left and right movement of the dispensing head permits reaching capability while up and down movement of the dispensing head serves to lower the cannulas into the wellplates for aspiration or dispensing of liquid. When combined with a wellplate support surface that features automatic loading and unloading of wellplates into a storage tower, the X, Y, Z movement of the dispensing head provides extended automated operation time, without human intervention.

In addition to providing extended reach to multiple wellplates, the multiple axis movement capability of the dispensing head and/or the support surface also permits automated loading and unloading of cannula arrays. The dispensing head can be moved to a cannula array storage area, the mounting system disengaged and cannula array released so that movement of the dispensing head serves to unload the given cannula array. Moving the dispensing head away from the cannula array releases it from the system and frees the dispensing head to receive a new, differently configured cannula array, as might be required during wellplate reformatting procedures. Next, the dispensing head is moved into alignment with the new cannula array and advanced to engage the cannula array plate with the quick-release mounting system of the dispensing head. With the new cannula array properly positioned in the mounting system by the alignment mechanism, the clamp may be actuated to secure the array onto the dispensing head and the dispensing head moved away from the storage area back to the working area where it will service the sample wellplates. The automated movement of the dispensing head not only reduces the need for human intervention, but also provides for more precise handling of the cannula array during loading and unloading than would be possible by human hands alone. It is believed that the precise movement of the dispensing head robotics can load and unload cannula arrays with improved alignment with the proper approach path of the quick-release mechanism resulting in fewer accidents.

It is an object of the present invention to provide a liquid dispensing handling system that provides for automated interchangeability of cannula arrays.

It is another object of the invention to provide a liquid handling system having a quick-release cannula array mounting system configured to permit rapid automatic or manual loading and unloading of a cannula array into operative engagement with a dispensing head.

It is another object of the invention to provide a liquid handling system having a dispensing head with a quick-release cannula array mounting system and a sample support surface wherein the liquid handling system is configured to provide for relative movement between the support surface and dispensing head in at least two dimensions.

It is another object of the present invention to provide a liquid handling system having a quick-release cannula array mounting system that provides for rapid and precise alignment of the cannula array with the fluid pathway of the dispensing head.

It is yet another object of the invention to provide liquid handling system having a quick-release cannula array mounting system that employs a sealing element between the cannulas and the fluid pathway of the dispensing head that provides fluid tight engagement over multiple cycles of use and array changeovers.

It is another object of the invention to provide liquid handling system having a quick release cannula array mounting system with means for urging separation of the cannula array from the dispensing head after release of the array by the mounting system clamp.

It is another object of the invention to provide a method of changing over a cannula array of a dispensing system that is simple and rapid, and may be conducted without significant interruption of the reliable operation of the dispensing system.

It is another object of the invention to provide a method of reformatting sample wellplates comprising automatically changing cannula arrays to maximize the capacity of wellplate servicing.

BRIEF DESCRIPTION OF THE DRAWINGS

The foregoing and other objects and advantages of the invention will be appreciated more fully from the following further description thereof, with reference to the accompanying diagrammatic drawings wherein:

FIG. 4 is a front-sectional view of a dispensing head of the liquid handling system with major components assembled;

FIG. 5A is a front view of the syringe body array of the dispensing head;

FIG. 5B is a top view of the syringe body array in the dispensing head overlying the cannula array;

FIG. 5C is a front view of the syringe body array of the dispensing head and a cannula array secured in the quick-release mechanism;

FIG. 6 is a side view of a longitudinal threaded rod;

FIG. 7A is a side view of a threaded bushing;

FIG. 7B is an end view of a threaded bushing; and

FIG. 8 is a side view of a clamping member

DESCRIPTION OF THE ILLUSTRATIVE EMBODIMENTS

Figure 1:
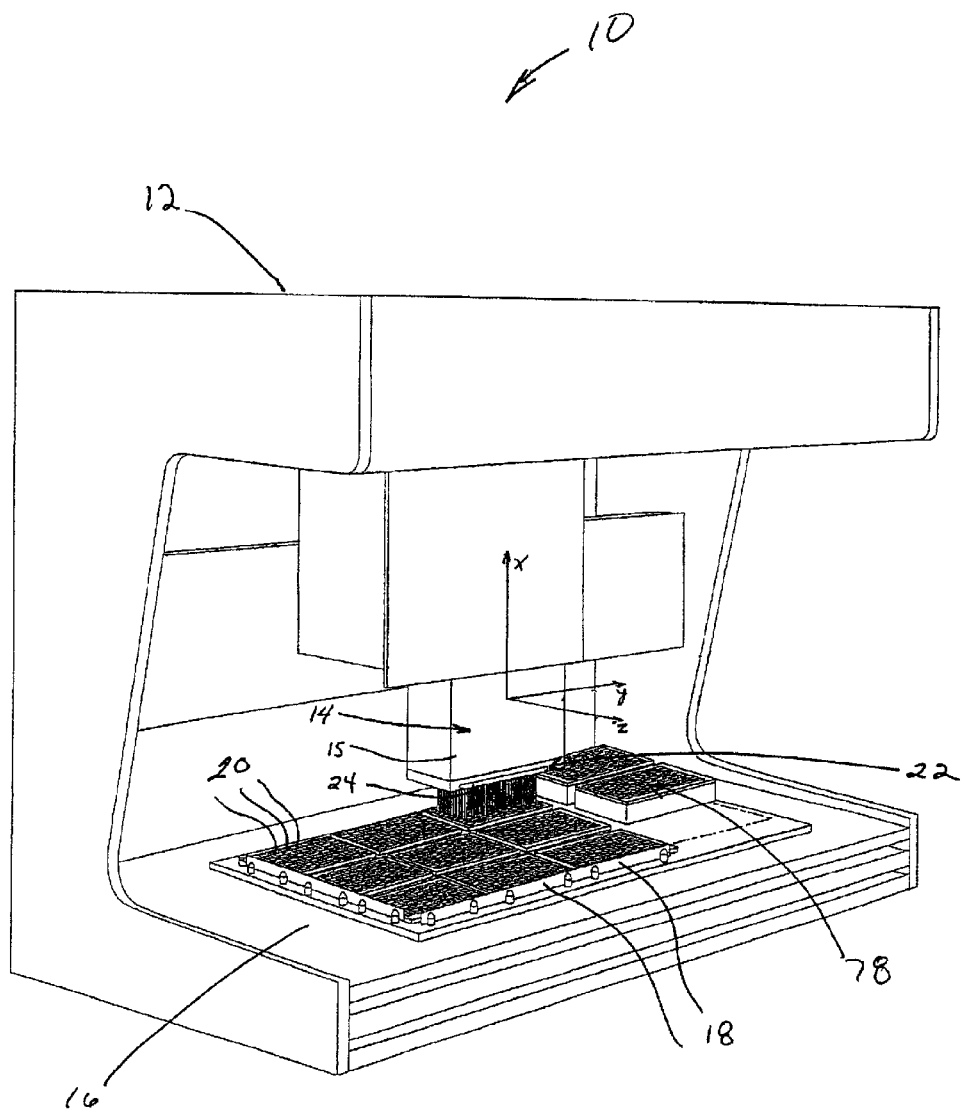
FIG. 1 shows a perspective view of a liquid handling system with a movable dispensing head having a quick-release cannula array mounting system.

FIG. 1 shows a perspective view of an automated liquid handling system according to the present invention. The liquid handling system 10 comprises a cabinet 12, dispensing head assembly 14 and sample support surface 16. The support surface 16 holds a plurality of well plates 18. The dispensing head assembly comprises several components configured to carry out aspiration of liquid from or dispensing of liquid into the wells 20 of an individual wellplate. Preferably, the dispensing head assembly 14 is configured to move in one, two or three dimensions to reach wellplates arranged on support surface 16. Alternatively or in addition to the dispensing head movement, the support surface 16 may be configured to move in one, two or three dimensions to provide relative movement between the components and increase flexibility of the dispensing operation. Whether the dispensing head, the support surface or both components are configured to move is not important as long as relative movement between the components is achieved to accomplish the cannula loading and exchange procedures discussed below, as well as any required dispensing operations.

Figure 2:
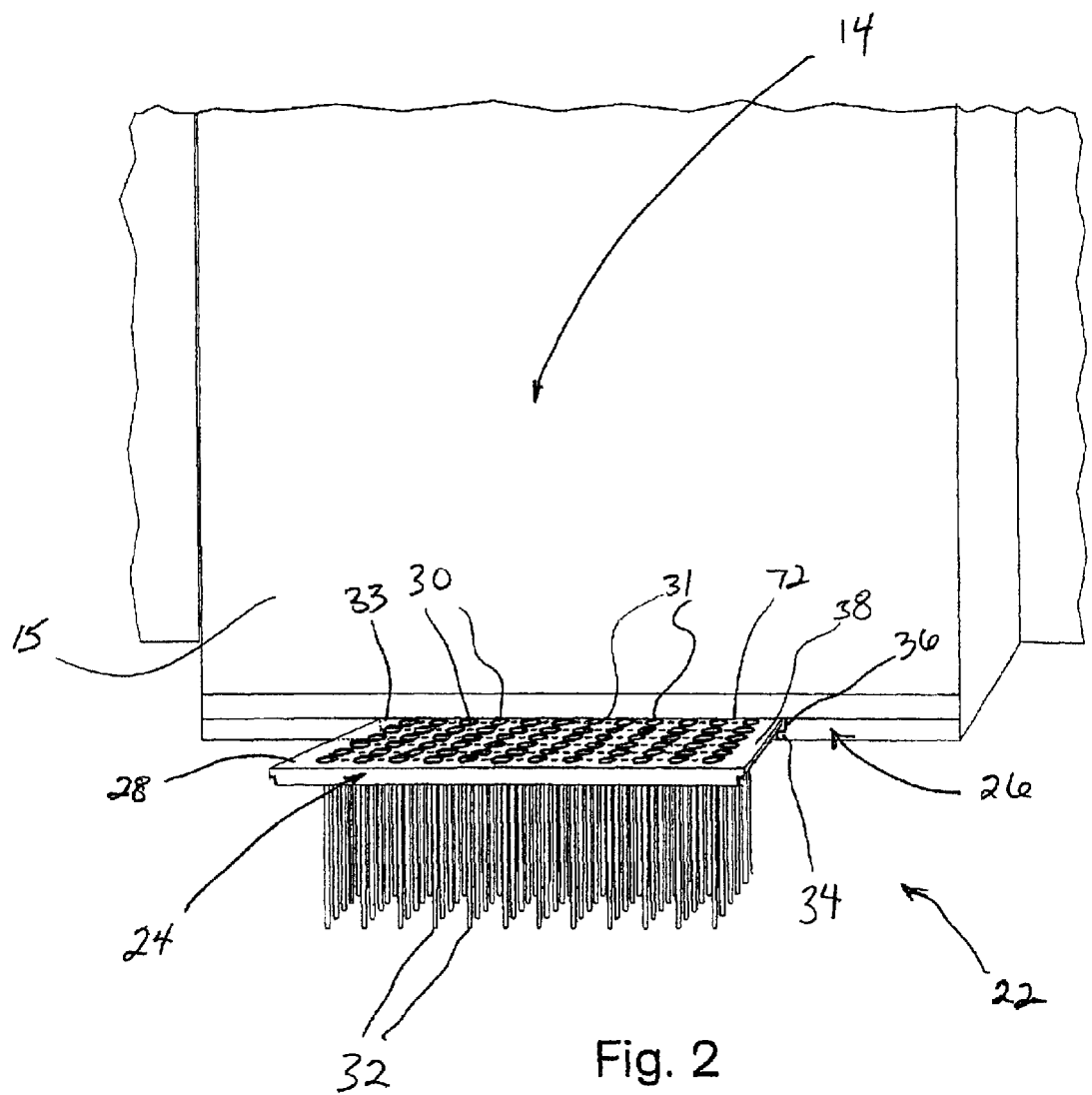
FIG. 2 is a detailed perspective view of a cannula being secured to a dispensing head.
Figure 3:
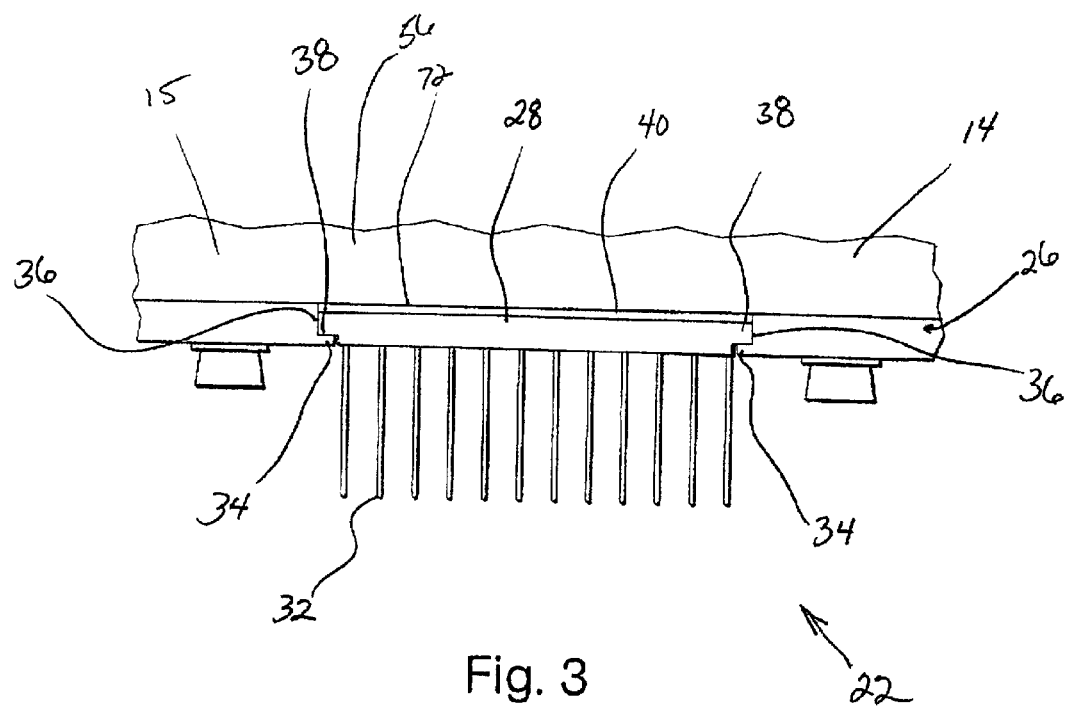
FIG. 3 is a front view of a cannula array loaded into the quick-release mounting system of the dispensing head.
Figure 9:
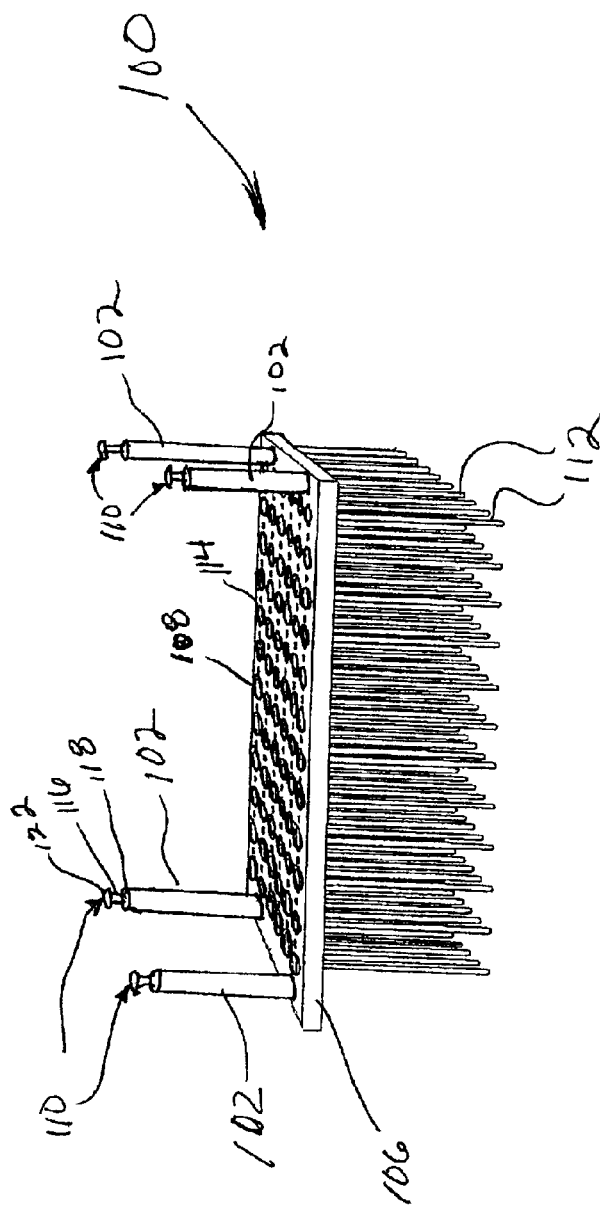
FIG. 9 is an isometric view of a cannula array equipped with pilot rods.

An important feature of the liquid handling system 10, incorporated in the dispensing head assembly 14, is a quick-release cannula array mounting system 22. In FIGS. 2 and 3, detailed views of a quick-release cannula array mounting system are presented. The quick-release mounting system 22 receives and holds a removable cannula array 24 that is releasably securable in the mounting system, which is located at the bottom of the dispensing head 14. The cannula array comprises a plate 28 having a plurality of passages 30 into which are affixed a plurality of dispensing tips or cannulas 32. The cannulas 32 may be made to be removable from the plate, but are preferably permanently mounted in passages 30 by such means as bonding with adhesive or brazing, such as with a gold-nickel braze. For durability with repeated use, both the cannulas 32 and the array plate are preferably made from rigid material such as stainless steel, though aluminum could also be used. Alternatively to the permanent cannulas, disposable plastic dispensing tips may be removably located in the cannula array plate 28.

As seen in FIGS. 2 and 3, a preferred embodiment of the quick-release cannula array mounting system may be configured for quick loading and unloading of the cannula array 24 by sliding the plate 28 into a L-shaped bracket 26 accessed from the front side 15 of the dispensing head assembly. The L-shaped bracket 26 has two opposing ridges 34 that, together with the bottom surface 72 of block 56, define slots 36 that extend longitudinally from the front side 15 of the bottom of the dispensing head inward. The plate 28 of the cannula array is slid into the slots 36 such that its outer periphery 38 engages the ridges 34 of the L-shaped bracket. After the plate has been inserted into the slots 36, a small clearance gap 40 on the order of about 0.030 inch preferably remains between the plate and bottom of the dispensing head to facilitate installation and alignment. Proper alignment of the loaded array is established by the configuration of the mounting system as is discussed in detail below. After loading of the plate, the mounting system may be activated, by means such as actuating a clamp, to secure the plate to the bottom of the dispensing head, also discussed in detail below.

FIG. 4 shows a sectional assembly drawing of the dispensing head 14. The dispensing head 14 comprises a syringe body array 42 into which is driven a plunger array 44 motivated by ball screw assemblies 46 driven by stepper motor 48. Beneath the syringe body array is the L-shaped bracket 26 that slidably receives the cannula array 24 and maintains it in alignment with syringe body array 42. Alignment between the fluid pathways defined by syringe bodies 58 of the syringe array 42 contained in the dispensing head 14 and the cannulas 32 of the loaded array 24 must be achieved to prevent fluid leaks that can interfere with dispensing or aspiration of liquids by the system. The arrangement of the L-shaped brackets 26 of the mounting system serves to guide the array 24 into alignment with the dispensing head 14.

The plunger array 44, shown in detail in FIG. 4, comprises a plate 50 having a plurality of individual plungers 52 extending perpendicularly away from the plate, corresponding in quantity and arrangement to the syringe bodies 58 of the syringe body array 42. The plungers 52 are cylindrical elements in sealed engagement with and slidable within the syringe bodies 58 of the syringe body array to cause displacement of the volume therein, which alters pressure to effect dispensing of liquid present in the cannulas 32 of the attached cannula array 24.

Preferably, the plungers are joined at one end to the plate 50 by a flexible or floating connection so that the plungers can move from side to side slightly when bumped or being aligned with the syringe body array. The plungers may be flexibly secured to the plate by a removable connector that captures a reduced diameter portion of a head shaped end of the plunger on the trough side of the plate. The removable connectors may comprise E-clips slid into a radial groove formed to define a head portion of the plunger. The neck of the head potion may be of a diameter that is slightly smaller than the through hole of the plate 50 in which it is captured to provide for some lateral movement of the plungers 52. The plungers are restrained from longitudinal movement relative to the plate by the connector, on one side of the plate, and a shoulder defining the head portion of the plunger on the other side of the plate.

Sealing engagement between the plungers and the syringe bodies may be created in a variety of ways. In a preferred arrangement, openings 43 to the syringe bodies (FIGS. 4–5C) are surrounded by sealing gaskets through which pass, in sealing engagement, plungers of the plunger array. The sealing engagement with the plungers serves to create a pumping action, suction or pressure when the plungers are moved up or down in the syringe bodies 58 to increase or decrease the syringe volume. The sealing gasket should surround each syringe opening 43 defining gasket openings sized to frictionally engage the plunger shafts 52. In a preferred arrangement, each opening 43 may have defined around it an annular space 41 slightly larger in diameter than the syringe body in order to receive a rubber o-ring gasket 45. The syringe O-ring gasket 45 may be secured in the annular space 41 by a rigid compression plate 39 (FIG. 4) releasably secured to the top of the syringe body array block 56 by screws 37.

The compression plate 39 has a plurality of through holes corresponding in size and arrangement to the openings 43 of the syringe bodies, in addition to several holes for the mounting screws 37. Securement of the compression plate serves to compress the gaskets slightly to create an airtight seal and to reduce the inside diameter of the O-rings to seal against the plunger shafts 52. The compression plate 39 is removable to permit the gaskets to be changed periodically when they become worn. Alternatively, the sealing gaskets may comprise a sheet of silicon rubber material compressed by the compression plate, having preformed holes corresponding to the number and arrangement of the syringe array. Also the sealed engagement between the syringe bodies and plungers may be created by pliable sealing element mounted to the distal ends of the plungers, similar to a conventional syringe plunger, sized to be in sealing engagement with the inside surface of the syringe bodies 58.

The plungers 52 are moved in the syringe bodies by movement of the plunger array plate 50 relative to the syringe body array 42. The plunger array plate 50 may be moved relative to the syringe body array by robotic equipment such as a ball screw assembly 46 driven by an electric motor 48. As shown in FIG. 4, such a system may comprise a plurality of lead screws 60 (system shown with two) joined to the plunger plate 50 by threaded engagement with a corresponding number of ball nuts 47 mounted to the plunger plate surface. Rotation of the lead screws 60 causes the ball nuts 47, and thus the plate 50 to advance up or down the lead screw shafts.

Synchronized rotation of the lead screws may be accomplished by electric motor 48. The motor is mounted on the liquid handling system to align motor shaft 57 and associated drive gear 51 with sprockets 53 mounted at the top of lead screws 60. A belt 63 transmits the rotational force from the drive gear 51 to the sprockets 53. Rotation of the sprockets serves to rotate the lead screws 60 in the ball nuts 47. As the ball nuts travel up or down along the length of the lead screw by way of their threaded engagement, the plunger array plate 50 to which the ball nuts are attached also is moved up or down (depending on the direction of rotation). Bearings 61 mounted at fixed points in the dispensing head receive the ends of the lead screws 60 in rotational engagement and serve to secure them in engagement. The bearings may be mounted in the syringe body array block 56 to locate the bottom of each lead screw and on the cross-arm 59 to locate the top of each lead screw. When the ball nut assembly is operated, the resulting vertical movement of the plunger array plate 50 relative to the syringe body array 42 serves to aspirate liquid into or dispense liquid from the attached cannulas 32.

The syringe body array 42 is shown in front view in FIG. 5A, top view in FIG. 5B and in front view with cannula array in FIGS. 4 and 5C. The syringe body array comprises a block 56 of rigid material such as aluminum or stainless steel, having defined therethrough a plurality of cylindrical passages that define the syringe bodies 58. The syringe bodies define fluid pathways of the dispensing head 14. The arrangement of each syringe body 58 and plunger 52 creates a small pumping chamber capable of negative or positive pressure. Syringe body block 56 also defines receptacles 62 for bearing inserts 61 that receive lead screws 60 employed to elevate and lower the plunger array 44 as mentioned above. The syringe block 56 also has defined therethrough four clamp channels 64 that slidably receive a clamping mechanism comprising clamping rods 68 (shown in FIG. 8), which are raised to provide clamping force to secure the cannula array 26 onto the dispensing head. On a bottom surface 72 of the block 56 is the L-shaped bracket 26 comprising two L-shaped arms 70 extending downward slightly from the block. The ridges 34 of the L-shaped arms serve to define slots 36 bounded by the bottom surface 72 of the block 56. Alternatively, the L-shaped bracket may comprise a plate mounted to the bottom of block 56 and having formed through its surface opposing L-shaped ridges 34 spaced to provide slots 36 into which the cannula array plate may slide.

Important to the successful operation of the quick-release cannula array mounting system is a sealing element to ensure that a fluid tight seal is established between the fluid pathway of the dispensing head and that of the cannula array. For proper aspiration and dispensing of liquids, each cannula must be sealed to the fluid pathway defined by a syringe body 58. Preferably, the sealing element is resilient and capable of multiple uses before requiring servicing or replacement durable yet effective sealing element. In a preferred embodiment, the sealing element comprises silicone rubber O-rings 31 (FIG. 2) located around each opening 30 of the cannula array plate 28. The O-rings are located in circular channels formed into the upper surface 33 of the cannula array plate 28, around each opening 30. The thickness of the O-rings is sized so that a portion of each seated O-ring protrudes slightly from the surface 33 of the plate. The protruding O-rings become compressed when the cannula array plate 28 is secured in the mounting system 22, clamped into engagement with the bottom surface 72 of the syringe array block 56. Slightly compressing the O-rings between the surfaces 33 and 72 creates a sealed, fluid tight engagement between each syringe body 58 and each corresponding cannula 32 to maintain the integrity of the fluid pathway of the dispensing head and the individual pumping chambers defined by the syringe bodies therein.

When the cannula array is released from the dispensing head, the O-rings separate cleanly from the surface 72 of the syringe block 56, so that another cannula array can immediately be loaded and clamped into position without any surface preparation. The O-rings remain in the circular channels around each opening 30 of the of the cannula array plate and their resiliency enables them to provide a sealing engagement for several future uses of the array plate, without servicing. When the O-rings eventually wear out, they can be removed from the circular channels and replaced with new rings.

Long-term mounting clamping of the cannula array and the compression of the O-rings may result in some sticking of the O-rings, and thus the cannula array, to the bottom 72 of syringe body array 56 after clamp release. The occasional tendency of the O-rings to stick is the result of compression of the rings and their form-fit contact with the syringe body bottom surface 72. To overcome the sticking force of the compressed O-rings after release of the clamp, a removal force may need to be applied to the cannula array to accomplish a full release. The removal force applied to the cannula array to move it away from the syringe body array may be applied by hand or may be provided by an ejection mechanism. In a preferred embodiment, the removal force may be automatically applied by a ejection mechanism comprising spring-loaded alignment pins (discussed in detail below) that are incorporated into the bottom surface 72 of the syringe body array that serve to apply a downward force on the cannula array plate 28, away from the syringe body block. The spring force selected for the alignment pins provides sufficient force to overcome O-ring sticking and urges the array plate 28 from the syringe block surface 72 when the clamp is released, but the spring force should be overcome by the advancing cannula array when the clamp is engaged to secure the array to the bottom of the syringe block. By way of example, using two spring loaded alignment pins to distribute the removal force on the cannula array plate 28, a spring providing force on the order of about 10 pounds may be used to preload each alignment pin.

As an alternative to individual O-rings, the sealing element may comprise a sealing mat of silicon rubber, which overlies the entire surface 33 of the cannula array and has holes cut out to correspond to the cannula openings 30. The sealing mat may be adhered to the cannula array plate 28 by such means as adhesive, and its resilience provides repeated sealing engagement through multiple changeovers of the cannula array through the quick-release system.

In another alternative arrangement, the sealing element may be incorporated into the cannulas themselves. Replaceable cannulas may be provided that are formed from a pliable material suitable for forming a gasket when compressed between the surface 33 of the cannula array plate 28 and bottom surface 72 of the syringe array. The cannulas may be formed with a raised flange at one end that becomes compressed between the array plate and syringe body bottom surface upon engagement. The cannulas are intended to be disposable after each use in light of the deformation that occurs in their flange area to seal the cannulas. Such cannulas may be assembled with the cannula array plate 28 by sizing the flange to be slightly larger than passages 30 so that the cannulas may be passed through the passages and retained by the flange from passing completely through the array plate. The cannulas may be replaced after use by advancing the cannulas back through the passages 30.

Sealing engagement between an individual syringe bodies 58 of the array block 56 and individual cannulas 32 of the cannula array 24 can be created despite the syringe body and the cannula plate being different array sizes as may occur when arrays are interchanged to expedite wellplate reformatting. For example, a 384 syringe body array may still operate with a 96 cannula array affixed to its bottom surface 72 by the quick-release system. The cannulas of a smaller sized cannula array 24 are arranged on the array plate 28 such that they each will align with a syringe body in sealed engagement as described above; however several surrounding syringe bodies will not be mated to a cannula and will operate freely without serving to aspirate or dispense a liquid through a cannula.

To facilitate alignment during loading of a cannula array, so that little or no human assistance is required, the quick release cannula array mounting system provides alignment guides, such as alignment pins 66 receivable into alignment recesses 76. In the L-shaped bracket mounting system embodiment, the alignment pins may be positioned to protrude from the bottom surface 72 of the syringe body array block 56, along slots 36, which is in proximity to the surface of the outer periphery 38 of a loaded cannula array. Alignment recesses 76, sized to closely receive the alignment pins are formed in the outer periphery 38 of the cannula array at locations that cause the array to be located in proper alignment with the syringe body array and dispensing head 14 when the pins engage the recesses. As a cannula array is advanced into slots 36 during loading, the slots guide the recesses 76 of the array into engagement with the alignment pins 66. Engagement of the pins into the recesses creates a positive stop, indicating alignment, that can be felt by an operator manually loading the array, or that can be detected by electrical sensors if loading is automated. The pins may be rigid projections or spring loaded roller balls that permit easy sliding of the cannula array into position until the spring loaded ball pops into the detent defined by alignment hole 76, arresting movement of the array and indicating alignment is reached. The clamp may then be engaged to secure the cannula array and, compressing the spring and driving the alignment pins upward into corresponding recesses in the process. As mentioned above, the spring-loaded alignment pins serve a second function by providing a disengagement force against the cannula array when the clamp is released in order to overcome any sticking of the O-rings that may occur due to prolonged sealing.

The positioning of the alignment pins and recesses also could be reversed so that the pins are formed on the cannula array and the holes are formed on the syringe body array surface. It also follows that other positive stop arrangements can be employed on the surfaces of the cannula array and syringe body array that are positioned to arrest relative movement between the surfaces when measured alignment is reached. Pins 66 and corresponding recesses 76 are but one example of a possible alignment mechanism. Other alignment mechanisms may be integrated into the L-shaped bracket embodiment and into other mounting system configurations as is discussed below.

After sliding the cannula array into the slots 36 defined by the L-shaped arms 70, the array is secured in position and sealing elements engaged by upward movement of a clamp that is part of the mounting system. In a preferred embodiment, the clamp comprises a plurality of notched clamping rods 68 (FIGS. 4–5C) that move upward or downward to secure or release the cannula array. The rods are moved by an actuator 80. Preferably four clamping rods are provided, arranged vertically and positioned to clamp areas adjacent each of the four corners of the cannula array plate. The actuator 80 need not be joined directly to the clamping rods but may operate to move a yoke 82 that joins to all the clamping rods so that they move simultaneously and in equal magnitude upon operation of the actuator 80. In their lowered position, a notch 74 of each clamping rod 68 aligns with the slots 36 defined by L-shaped arms 70. Therefore, when the periphery 38 of the cannula array slides into slots 36, it also slides into notch 74 of each rod. The notch 74 is sized to receive the thickness of the cannula array plate 28. To lock the cannula array in place against the bottom surface 72 of block 56, the clamping rods 68 are moved upward in unison by yoke 82. The cannula array plate 28, which has been captured within the notches 74, moves upward into engagement with the bottom surface 72 of syringe array block 56. Four clamping rods 68 are believed to provide effective spacing to support and secure the plate 28 by creating four small areas of engagement around the outer periphery 38, adjacent the four corners of the plate.

Alternatively, more or fewer clamping rods could be employed to engage the cannula array at various points or surface. Alternatively, the clamping rods could be substituted by other positive engagement structural members to effect clamping. It is important that, regardless of the clamp member configuration, the clamp engage the array plate 28 at one or more points to provide an even and effective clamping force that will not only secure the plate, but also insure sealed engagement between the cannulas and syringe bodies. By way of example, in the preferred embodiment using four clamping rods, a pneumatic actuator is pressurized to 50 psi to achieve approximately 200 lbs of clamping force to secure the cannula array.

The clamping rods may be actuated by any dynamic element capable of causing sufficient displacement of the rods to overcome the clearance gap 40 and cause secure engagement with the bottom surface 72. Preferably, the actuator can be remotely or automatically engaged to raise the clamping rods. Ideally, the actuator can be operated via an electric signal that can be controlled by and integrated with a computer-based system controller using customized software that energizes different components of the system in sequential fashion to accomplish automated operation of the dispensing system. In this configuration, the quick-release mounting system can be operated by command of the computer software to release clamping force on the cannula array after the dispensing head 14 has been moved to a cannula array storage area 78 (shown in FIG. 1) to permit release of a cannula array. Next in the loading sequence, the computer controller signals the system robotics to move the dispensing head 14 to the position of a new cannula array maintained in the storage area 78 and position the head to slide over the cannula array, as shown in FIG. 2, for loading, and then signal the actuator to clamp the array into place. A preferred actuator mechanism for the clamping rods is a pneumatic cylinder actuator 80. Alternative remotely controllable actuators include electric solenoids, hydraulically actuated cylinders or threaded rods driven by electric stepper motors. Also, a variety of manual mechanical means can be employed to displace the clamping members the required distance to secure the cannula array, although such systems would not be integrated into a computer controlled network preventing complete automation of the system. As mentioned above, the cannula arrays also may be changed over manually by an operator. In manual changeover procedures, the dispensing head need not be moved to the storage area 78. Rather, the operator need only activate the actuator to unclamp the existing array, manually grasp the array, disengage it from the alignment pins and slide it out from the L-shaped bracket. A new array may be manually loaded in reverse order of those steps. Manual operation is also expedited by the system due to the self-alignment provided by the alignment mechanism, actuated clamping, and reusable sealing element that need not be serviced with each changeover.

To insure proper clamping force of the cannula array is applied by the actuator, one or more springs of known spring constants may be inserted between the contact surfaces 86 of the yoke 82 and clamping rods 68 to regulate the amount of upward force transmitted from the yoke to the rods, as shown in FIG. 4. Bellville spring washers 84 may be used as the spring elements. When the actuator is actuated to clamp the cannula array, the contact surfaces 86 of the yoke 82 will push upward on the Bellville springs 84, compressing them slightly and causing movement of the clamping rods 82 as the Bellville springs push against contact surfaces 86 of the rod. However, the displacement and clamping force transmitted by the rods 68 to the cannula array 24 is primarily determined by the spring force provided by the spring washers. For example, if the amount of displacement offered by the actuator 80 is excessively great such that it would damage the cannula array by applying excessive clamping force, the Bellville spring washers 84 can absorb the excessive displacement by compressing slightly, while maintaining an acceptable force against the contact surfaces 86 that results in an acceptable clamping force against the cannula array. Additionally, the Bellville spring washers permit a floating engagement with the clamping rods when in the extended (released) position to help avoid damage of system components when clamping forces are applied, if the cannula array or other pieces happen to become misaligned.

In use, the automated liquid handling system may be operated by the following methods. To remove and install a cannula array using the quick-release mounting system, the actuator is operated to move the clamping rods 68 downward to release the clamping engagement between the notches 74 and the outer periphery 38 of the cannula plate 28. The actuator may be activated directly by an operator or automatically by a remote electrical signal from the system controller such as a computer and appropriate computer software. After the clamping system has been released, the cannula array plate may be slid out from the slots 36 by manually pulling the plate toward the front 15 of the dispensing head. The new cannula array may be slid into the slots 36 until positive engagement occurs with the alignment pins 66 of the mounting system engaging the alignment recesses 76 in the array plate. Engagement of the alignment mechanism ensures proper alignment of the array before it is securely clamped in position. After, loading the cannula array, the clamp is operated to engage and lift the array plate 28 into engagement with the dispensing head and apply an appropriate clamping force to provide sealed engagement. The dispensing head then may be positioned over a wellplate and aspiration and dispensing procedures commenced.

In fully automatic operation, the dispensing head first may be moved to the cannula array storage area 78 and lowered to rest the array on a suitable support surface. After the clamp is released (lowered by the actuator), the dispensing head is moved in a rearward direction (along the z-axis) to cause relative movement of the array toward the front of the dispensing head so that it slides out from the slots 36 and is released from the dispensing head. The dispensing head then is repositioned to accept a new cannula array. The dispensing head is moved forward, along the z-axis, maintaining positions along the x and y axes, so that the cannula plate will be received in slots 36 of the L-shaped brackets 26. The dispensing head moves forward the required amount to fully accept the plate in the quick-release system. Alternatively, the support surface may be configured with robotics to move along the necessary axes relative to the dispensing head in order to load the array. Alignment pins 66 engage with alignment recesses 76 upon completion of loading to ensure proper alignment of the array plate. Optionally, sensors may be employed with the alignment pins to indicate by electrical signal to the system controller (or to an operator if manual loading is contemplated) that the array has been successfully aligned and is ready for mounting. After loading of the plate, the controller signals the actuator to raise the clamping bars to secure the cannula array in place. Next, the controller repositions the dispensing head from array plate storage area 78 to the area of the wellplates 18 on the support surface 16 and initiates aspiration and dispensing operations.

Variations of the cannula array securement mechanism compatible with two-dimensional relative movement between the dispensing head 14 and the wellplate support surface 16 are possible. In a two-dimensional system, relative movement between the components is limited to the up and down (y-axis) and either left/right (x-axis) or front to back (z-axis) axes. For fully automated cannula array change over procedures, movement of the dispensing head or support surface along the x or z-axis may be needed for dropping off and picking up cannula arrays at different positions in a storage area 78. Therefore, it may be desirable to have movement needed for securing the cannula array occur along the y-axis, during up and down movement, without requiring lateral movement. To achieve securement in such systems, the L-shaped bracket may be eliminated in favor of a system that utilizes several pilot rods mounted on the cannula array that are located to engage the clamping rods and align the cannula array with the fluid pathway of the dispensing head.

The embodiments of FIGS. 9–11B use a cannula array 100 having pilot rods 102 rather than an L-shaped bracket to achieve alignment of the array with the dispensing head. The pilot rods 102 engage directly with the clamping rods to form a connection between the dispensing head and cannula array. As with the cannula arrays discussed above, the cannula array is comprised of a plate 106 having a plurality of passages 108 corresponding to the individual cannulas 112. Sealing elements such as O-rings 114 are positioned at the passages to form a seal with the bottom of the syringe body array, as with the previous embodiment. The pilot rods 102 are rigid members formed from aluminum, stainless steel or rigid polymer extending from the plate in a perpendicular relationship. They are secured at one end to the plate by such means as threaded fastener screwed through the plate into the rod or they may be secured by welding. At the other end of the rod is formed a cap shaped head 110 for engaging the locking mechanism. The cap-shaped head 110 is configured for easy grasping by mechanical means. In the example shown in FIGS. 9–11B the head 110 comprises a neck portion 116 of reduced diameter, having a cap end 122 of increased diameter, preferably finished with sloped sides presenting a shape similar to a cap. The other end of the neck portion joins to the rest of the pilot rod 102 at shoulder 118, which defines an increase in diameter to that of the remainder of the pilot rod. The neck portion 116 of the cap head 110, bounded by two larger diameter areas (shoulder and cap head) provides a section that is easily engaged by mechanical means. Mechanical clamps close around the neck portion and the rounded cap portion provides an underside surface 124 against which a mechanical clamp may become leveraged to transmit an axial force.

Figure 10A:
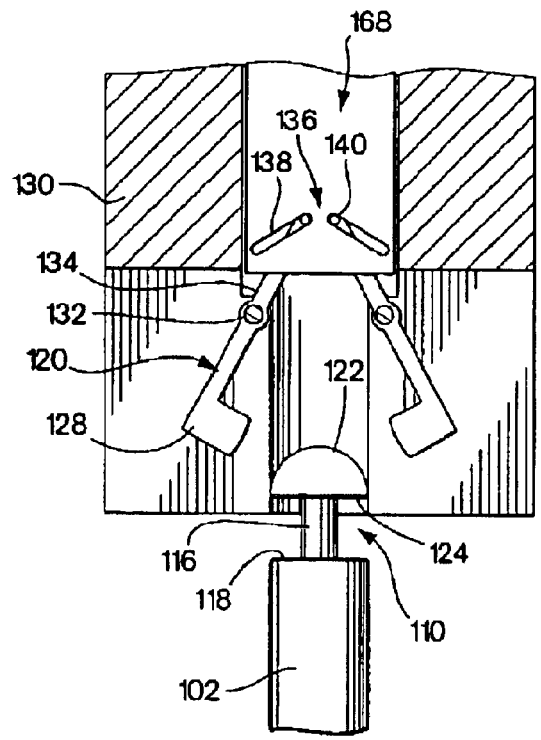
FIGS. 10A–11B are front sectional views of quick-release lock mechanisms for securing the cannula array to the mounting system.
Figure 10B:
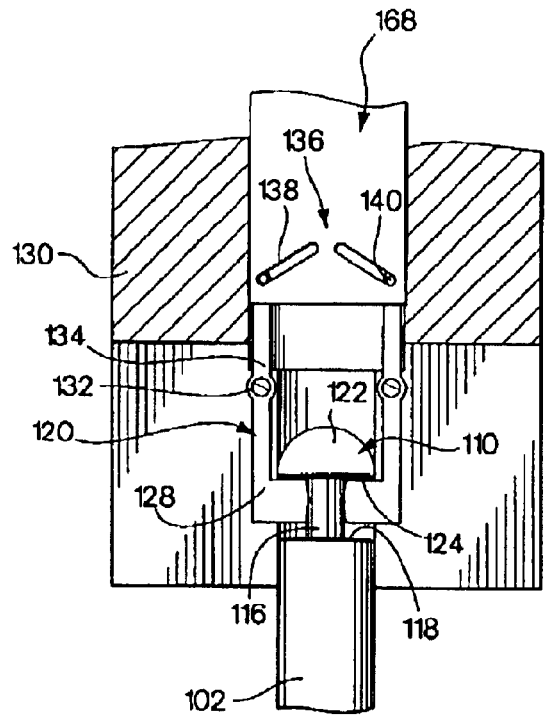

In the example of FIGS. 10A–10B, a quick-release lock mechanism, shown in a sectional side view comprises a hinged clamp 120 that is hinged to the end of modified clamping rod 168. The modified clamping rod comprises an outer sleeve 130 that provides a mounting point for the hinged clamp. The hinged clamp 120 comprises two opposed claw arms 128 each rotatably connected to a pivot point 132. After the pivot point connection 132, the arms extend to a relatively straight leverage portion 134 that is joined to the clamping rod. A slidable connection 136 having ramped slots 138 in which connecting pins 140 at the distal end of the leverage portions 134 may slide is provided at the bottom of clamping rods 168 in place of notch 74 of the clamping rods 68 of the previous embodiment. When the clamping rods 168 are lowered by the actuator 80, the connecting pins are urged up the ramp slots 138 of the slidable connection, causing the ends of the leverage portions 134 to converge. When the leverage portions converge, the claw arms diverge by virtue of the pivot point connection 132.

Clamping rods move relative to the outer sleeve 130 and the pivot points 132 mounted thereon for a limited range of travel so that rotation about the pivot point results from movement of the clamping rods. After a limited range of relative movement, sufficient to permit connection pins to travel the extent of slots 138, the clamping rods and sleeve 130 move in unison throughout the remainder of clamping rod travel.

With the clamping rods in a lowered position, the claw arms 128 are spread apart and ready to receive the cap head 110 of the pilot rods 102. As the dispensing head lowers over the cannula array (or the support surface moves upward to the dispensing head), the pilot rods are received in the outer sleeve 130, which serves as a guide to align the array with the dispensing head. Insertion of the pilot rods into the outer sleeve is accomplished by operator judgment, if loaded manually, or by movement of robotics that are computer and capable of monitoring x-y-z-axis positioning of the equipment. When the clamping rods are raised, the connecting pins 140 slide down the ramped slots 138, causing the leverage portions 134 to diverge apart. As the leverage portions rotate apart about pivot point 132, the claw portions 128 of the arms converge to capture the cap heads of the pilot rods. After capturing the cap heads, the outer sleeves then move in unison with the clamping rods, which continue upwards to pull the cannula array 100 into engagement with the bottom surface 72 of the syringe body block 56.

Figure 11A:
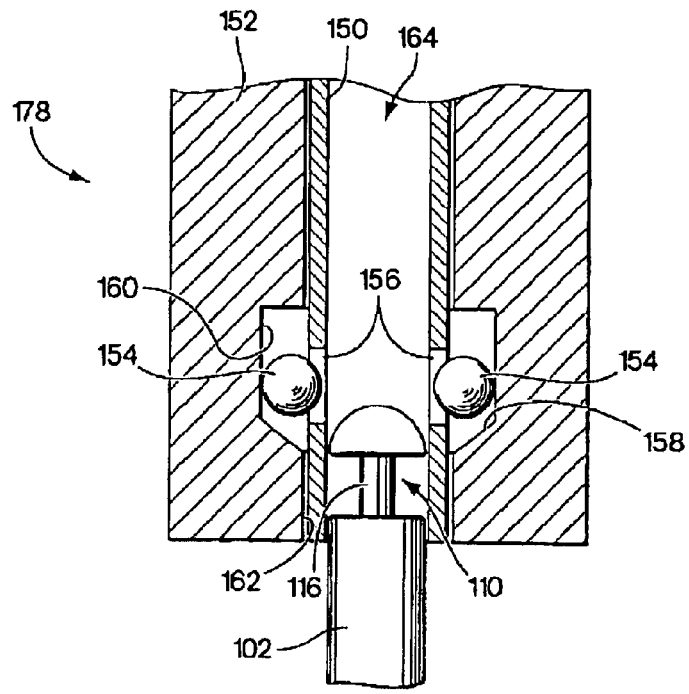
Figure 11B:
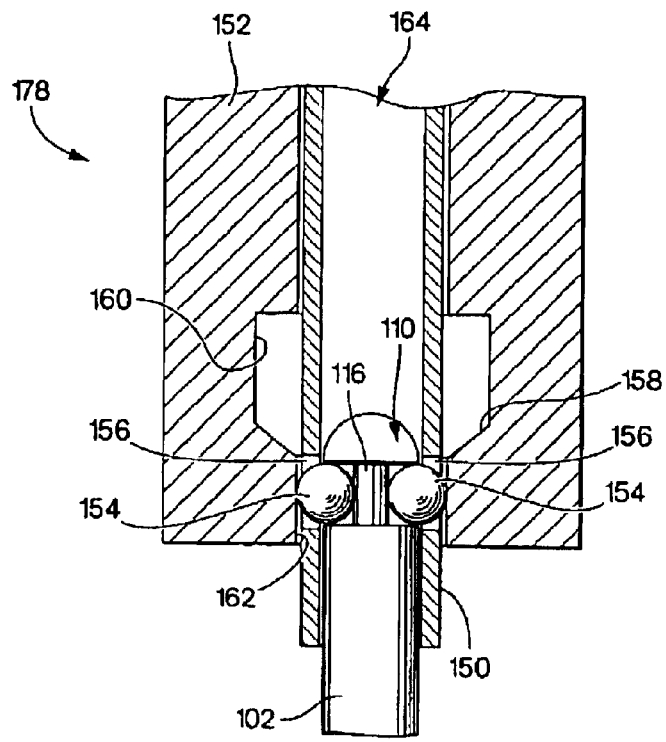

Another alternative quick release system for cannula array securement is shown in FIGS. 11A and 11B. As with the above-described embodiment, the present embodiment interfaces with a cannula array 100 having a plurality of pilot rods 102 (FIG. 9) and is capable of automatically loading the cannula array with relative movement between the dispensing head and the support surface in a single dimension. The quick-lock embodiment shown in FIGS. 11A and 11B is similar in configuration and operation to a conventional quick-connect compressed air coupling using a retractable sleeve method of connection. The clamping rods 178 comprise a double sleeve arrangement. An inner sleeve 150 has an inside diameter sized slightly larger than the pilot rods 102 so that the pilot rods can be received inside the sleeves. Each inner sleeve 150 also retains a plurality of locking balls 154 retained in ball ports 156 formed through the sidewall of the sleeve 150. The locking balls are rigid, similar to ball bearings and may be formed from a material such as stainless steel. The ports are sized slightly smaller than the diameter of the balls so that the balls can protrude through the ports but not pass through completely. When protrude through the port and into hollow interior cavity 164 of inner sleeve 150, the locking balls can engage the necked portion 116 of the cap head 110 of the pilot rods 102 to create a positive engagement between the cannula array and clamping rods.

The locking balls 154 can be driven selectively into and released from the ball ports by outer sleeve 152. The outer sleeve is slidably mounted over the inner sleeve over the area of the locking balls. The inside surface of the outer sleeve is configured to have a ramp 158 transitioning from a larger inside diameter region 160 to a smaller diameter region 162. In a release/loading position shown in FIG. 11A, the outer sleeve is in a lowered position, so that the larger inside diameter portion 160 corresponds to the location of the locking balls 154. The larger inside diameter of region 160 provides clearance to permit locking balls to slide out of substantial engagement with ball ports 156, yet confines the balls sufficiently to maintain them in contact and aligned with the ports. In this position, pilot rods 102 are free to pass through inside cavity 164 of inner sleeve for loading or unloading. The cavity serves as a guide to direct the pilot rods and thus the cannula array into alignment with the dispensing head as the support surface or dispensing head are moved relative to the other to conduct loading.

The locked configuration of the quick-release mechanism is shown in FIG. 11B. In the locked position, the outer sleeve 152 is moved upward relative to the inner sleeve 150 and locking balls 154 located in ball ports 156. As the outer sleeve moves upward, ramps 158 engage balls 154 directing them inward into full engagement with ports 156 as the smaller diameter region 162 is finally aligned with the balls. In this position, though the balls 154 are in full engagement with the ports 156, the ports are of a diameter that is slightly smaller than the diameter of the balls so that they protrude into the inner cavity 164 but do not pass all the way through the port. Protruding balls 154 thus are positioned to engage the necked region 116 of the pilot rods 102 in the cavity 164. After the pilot rods have been engaged by the locking balls, inner and outer sleeves 150 and 152 are moved in unison to raise the cannula array 100 into engagement with the bottom of the syringe body array. The relative movement of the inner and outer sleeves of the clamping rods 178 may be provided by separate actuators or by a single actuator in combination with mechanical linkage that ties the movement of one sleeve to the other at various points through their relative strokes.

Another alternative quick-release embodiment loadable with movement in one dimension may be derived from the L-shaped bracket system described above. The alternate embodiment (not shown) is similar in that it uses clamping rods 68 having notches 74. However, the alternate embodiment eliminates the L-shaped bracket, which involves loading of the cannula array by sliding into slots 36. Pilot rods, discussed with the embodiments of FIGS. 10A–11B, also are not necessary with the present embodiment. Rather, the clamping rods 68 are configured to rotate along their longitudinal axes so that the notch 74 can be rotated into engagement with the cannula array plate during loading and rotate out of engagement to release the array plate. In operation, the dispensing head is moved into position directly over the cannula array plate 28 with the notches 74 of clamping rods rotated outward, away from the plate. The dispensing head 14 is then lowered to the height necessary for the notches to align with the thickness of the array plate. Once aligned, the clamping rods are rotated to direct the notches inward to engage the plate 28. The clamping rods may then be elevated to lift the cannula array into engagement with the bottom 72 of the syringe body array block 56. To release the cannula array, the clamping rods are lowered to disengage the cannula array from the syringe body block. Next, the clamping rods are rotated so that the notches 74 face outward and disengage the cannula array plate 28. The clamping rods may be rotated by a stepper motor and belt system similar to the ball screw assembly 46 discussed above.

The quick-release cannula array mounting system facilitates reformatting operations especially when reformatting over two arrays sizes is contemplated. To accomplish such reformatting procedures the liquid handling system of the present invention can automatically change the cannula array to the next higher array size after larger size array wellplates have been filled from several smaller array plates. Initially, a first, small size cannula array, such as a 96-cannula array is secured to the dispensing head by the above procedures. The 96 cannula array is used to aspirate liquid samples from four existing 96 wellplates, then the samples are dispensed into one 384 wellplate, thereby reducing the number of wellplates required for storage from four to one. To further reformat four 384 wellplates to a single 1536 wellplate the 96 cannula array may be changed over to a second, larger cannula array (a 384 cannula array) to expedite the reformatting process by reducing the number aspiration, dispensing and cleansing steps performed by the dispensing head.

The positioning and magnitude of movement of the dispensing head and or sample support surface required for self-loading of the cannula array described above is carried out by robotics comprising electromechanical drive systems controlled by a computer. The computer software is capable of receiving sequenced movement instructions for the drive mechanism that move the dispensing head. Range of motion and positioning information on the x-y-z coordinates can be programmed in the software to move the dispensing head to the required locations in the required sequence to carry out the steps outlined above for loading and unloading the array and carrying out reformatting operations.

It should be understood that the foregoing description of the invention is intended merely to be illustrative thereof and that other modifications, embodiments and equivalents may be apparent to those skilled in the art without departing from its spirit.

What is claimed is:

1. A liquid handling system comprising:
   a dispensing head;
   a sample support surface;
   a quick-release mounting system comprising a releasable clamp capable of releasably securing a cannula array to the dispensing head, the quick-release mounting system further comprising an alignment mechanism having guides comprising spring-loaded alignment pins configured to engage with corresponding recesses on a cannula array to properly locate the cannula array when loaded into the system; and
   the handling system being configured to provide for relative movement between the dispensing head and sample support surface in at least two dimensions.

2. A liquid handling system as defined in claim 1 wherein the handling system is configured to provide for relative movement between the dispensing head and support surface in three dimensions.

3. A liquid handling system comprising as defined in claim 1 wherein the dispensing head is movable in three dimensions.

4. A liquid handling system as defined in claim 1 wherein the dispensing head comprises at least one fluid pathway that is selectively pressurizable.

5. A liquid handling system as defined in claim 4 wherein the dispensing head comprises a fluid pathway defined by at least one syringe body capable of aspirating and pressurizing fluid.

6. A liquid handling system as defined in claim 4 wherein the dispensing head comprises a fluid pathway selectively pressurized by an external pressure source.

7. A liquid handling system as defined in claim 4 further comprising a cannula array that comprises a plate having a plurality of openings formed therethrough and cannulas extending from one side of the plate at each opening and the other side of the plate being configured for engagement and communication with the fluid pathway of the dispensing head.

8. A liquid handling system as defined in claim 7 wherein the cannulas are fixedly attached to the plate at each opening.

9. A liquid handling system as defined in claim 7 wherein the releasable clamp is configured to engage the cannula array at least partially around the periphery of the cannula array plate.

10. A liquid handling system as defined in claim 7 further comprising a sealing element between each cannula and the fluid pathway of the dispensing head that creates a fluid tight seal when a cannula array is secured to the dispensing head.

11. A liquid handling system as defined in claim 10 wherein the sealing element comprises O-ring gaskets surrounding each opening of the cannula array plate.

12. A liquid handling system as defined in claim 10 wherein the sealing element comprises a sealing mat of resilient material overlying the cannula array plate with openings defined therethrough corresponding to the openings of the array plate.

13. A liquid handling system as defined in claim 10 wherein the sealing element is integrated into a portion of the cannulas.

14. A liquid handling system as defined in claim 13 wherein the cannulas are removably located by the cannula plate and comprise disposable plastic dispensing tips.

15. A liquid handling system as defined in claim 7 further comprising a plurality of pilot rods extending from the cannula array plate and engageable with the releasable clamp of the mounting system.

16. A liquid handling system as defined in claim 15 wherein the releasable clamp further comprises clamping rods corresponding in number to the pilot rods and having hinged clamps that releasably engage cap head portions of the pilot rods.

17. A liquid handling system as defined in claim 15 wherein the releasable clamp further comprises clamping rods corresponding in number to the pilot rods, each having a cavity that receives the pilot rods and having locking balls that are driven radially inward by sliding movement of an outer sleeve about the clamping rod to capture the pilot rods in the cavities.

18. A liquid handling system as defined in claim 1 further comprising a controller configured to provide automated control of the relative movement between the dispensing head and support surface.

19. A liquid handling system as defined in claim 18 wherein the controller controls operation of robotics that move the dispensing head.

20. A liquid handling system as defined in claim 18 wherein the quick-release mounting system is operated automatically under command of the controller.

21. A liquid handling system as defined in claim 1 wherein the releasable clamp is actuated remotely.

22. A liquid handling system as defined in claim 1 wherein the releasable clamp is actuated manually.

23. A liquid handling system as defined in claim 1 wherein the releasable clamp is actuated by pneumatic pressure.

24. A liquid handling system as defined in claim 23 wherein the pneumatic pressure actuates the clamp through a pneumatic solenoid joined to the clamp.

25. A liquid handling system as defined in claim 1 wherein the quick-release mounting system comprises at least one L-shaped bracket providing slots on the dispensing head arranged to slidably receive the cannula array.

26. A liquid handling system as defined in claim 1, further comprising a clamp actuating mechanism and at least one spring positioned between the releasable clamp and the clamp actuating mechanism to control the amount of clamping force applied to the cannula array by the clamping mechanism.

27. A liquid handling system as defined in claim 1 wherein the releasable clamp is configured to become aligned with a cannula array by relative movement between the dispensing head and support surface in a single dimension.

28. A liquid handling system as defined in claim 1 further comprising: an ejection mechanism configured to separate a cannula array from the dispensing head when the releasable clamp is released.

29. A liquid handling system as defined in claim 28 wherein the ejection mechanism comprises a spring-loaded projection.

30. A liquid handling system comprising:
a dispensing head;
a sample support surface;
a Quick-release mounting system comprising a releasable clamp capable of releasably securing a cannula array to the dispensing head, wherein the quick-release mounting system further comprises at least one L-shaped bracket providing slots on the dispensing head arranged to slidably receive the cannula array, wherein the slots of the at least one L-shaped bracket have alignment pins configured to engage corresponding alignment recesses on the cannula array; and
the handling system being configured to provide for relative movement between the dispensing head and sample support surface in at least two dimensions.

31. A liquid handling system comprising:
a dispensing head;
a sample support surface, the handling system being configured to provide for relative movement between the dispensing head and sample support surface in at least two dimensions;
a quick-release mounting system comprising a releasable clamp capable of releasably securing a cannula array to the dispensing head, wherein the releasable clamp is configured to become aligned with a cannula array by relative movement between the dispensing head and support surface in a single dimension; and
a cannula array storage area on the support surface to which is transferred cannula arrays from the dispensing head by relative movement between the dispensing head and the support surface in a second dimension that is different from the first dimension used to connect the cannula array.

32. A method of automatically changing a cannula array for a liquid handling system comprising:
providing a liquid handling system having a dispensing head with a quick-release cannula array mounting system, a sample support surface configured to support at least first and second cannula arrays wherein the handling system is configured to provide for relative movement between the dispensing head and support surface in at least two dimensions;
moving the dispensing head of the liquid handling system to an area on the support surface;
releasing a first cannula array from the quick-release mounting system;
moving the dispensing head to withdraw the mounting system from the cannula array, leaving the first cannula array on the support surface;
moving the dispensing head to a second cannula array on the support surface and advancing the dispensing head to locate the second cannula array in line with the mounting system of the dispensing head; and
actuating the mounting system to secure the second cannula array to the dispensing head.

33. A method of changing a cannula array in an automated liquid handling system as defined in claim 32 wherein each of the steps are controlled by a computer controller operating software customized to include the parameters for the required steps.

34. A method of changing a cannula array on an automated liquid handling system as defined in claim 32 wherein the cannula array is secured in the quick-release mounting system by a clamp that is actuated by the controller.

35. A method of reformatting a first wellplate having a first array format to a second wellplate having a second array format and a third wellplate having a third format comprising:
providing a liquid handling system having a dispensing head with a quick-release cannula array mounting system and a sample support surface and being configured to provide relative movement between the support surface and dispensing head in at least two dimensions, a first cannula array having a first array format, second cannula array having an intermediate array format, and a third array having a large array format,
loading a cannula array having a first array format into the quick-release mounting system
moving the dispensing head to be aligned with a wellplate having a first array format;
aspirating liquid from the first wellplate into the cannula array;
moving the dispensing head to a wellplate having a second array format, positioning the first cannula array into the second wellplate and dispensing the liquid into wells of the wellplate;
repeating the above steps aspirating liquid from other wellplates having a first array format, until the wellplate having a second array format is filled,
automatically exchanging the first cannula array for a second cannula array having a second array format by releasing the first cannula array and moving the dispensing head to the second cannula array and securing it into engagement with the quick release mounting system of the dispensing head;
moving the dispensing head to the second wellplate;
aspirating sample liquid from the second wellplate into the second cannula array; and
moving the dispensing head to a third wellplate having a third array format, dispensing a sample liquid from the second cannula array to the third wellplate, then repeating the above steps to fill the wells of the third wellplate from the second cannula array.

36. A method of reformatting a wellplate as defined in claim 35 wherein the first wellplate is configured to have 96 wells, the second wellplate is configured to have 384 wells and the third wellplate is configured to have 1,536 wells.

* * * * *